United States Patent [19]

Cymbalisty et al.

[11] 4,328,710
[45] May 11, 1982

[54] HOMOGENIZER/SUBSAMPLER FOR TAR SAND PROCESS STREAMS

[75] Inventors: Lubomyr M. O. Cymbalisty; Robert C. Shaw, both of Edmonton, Canada

[73] Assignees: Petro-Canada Exploration Inc., Calgary; Her Majesty the Queen in right of the Province of Alberta, Government of the Province of Alberta, Department of Energy and Natural Resources, Alberta Syncrude Equity, Edmonton; PanCanadian Petroleum Limited, Calgary; Esso Resources Canada Ltd., Calgary; Canada-Cities Service, Ltd., Calgary; Gulf Canada Resources Inc., Calgary, all of Canada

[21] Appl. No.: 250,241

[22] Filed: Apr. 2, 1981

Related U.S. Application Data

[62] Division of Ser. No. 90,923, Nov. 5, 1979, Pat. No. 4,284,360.

[51] Int. Cl.³ .............................................. G01N 1/20
[52] U.S. Cl. ................................. 73/863.86; 366/140
[58] Field of Search ........... 73/863.86, 863.81, 863.83, 73/863.43, 863.45; 366/140

[56] References Cited

U.S. PATENT DOCUMENTS

| | | | |
|---|---|---|---|
| 1,351,352 | 8/1920 | Stevens | 366/149 |
| 2,038,221 | 4/1936 | Kagi | 366/266 |
| 2,843,169 | 7/1958 | Stein | 366/140 |
| 3,106,096 | 10/1963 | Broerman | 73/863.12 |
| 3,189,080 | 6/1965 | Overcashier | 366/270 |
| 3,460,811 | 8/1969 | Hugli | 366/270 |
| 4,132,666 | 1/1979 | Chikatsu | 366/249 |

OTHER PUBLICATIONS

Strahman Sampling Valve, Fig. SV-700, (An Advertizing Brochure) Nicolet Ave. Florham Park, N.J. 2 pages.

Primary Examiner—S. Clement Swisher
Attorney, Agent, or Firm—Ernest Peter Johnson

[57] ABSTRACT

An apparatus and process are described for homogenizing and subsampling process streams such as those present in the hot water extraction process for recovery of bitumen from tar sand. Such streams contain widely variable proportions of heavy oil, water, and solids. To obtain a representative analysis-size subsample from such a stream, a bulk sample is taken into a cylindrical open-topped vessel containing a coaxial cylindrical draft tube spaced from the internal wall of the vessel. A head element closes and seals the top of the vessel. An impellor extending into the draft tube through the head element is actuated to circulate the bulk sample along an elliptical flow path within the vessel. The vessel contents are maintained in a pressurized condition by the introduction of inert gas. A subsample is taken by mechanically opening and closing a sample port extending through the side wall of the vessel and communicating with the flow path; the subsample is thus taken while the bulk sample is in motion and the components of the mixture are in a homogenized condition.

1 Claim, 5 Drawing Figures

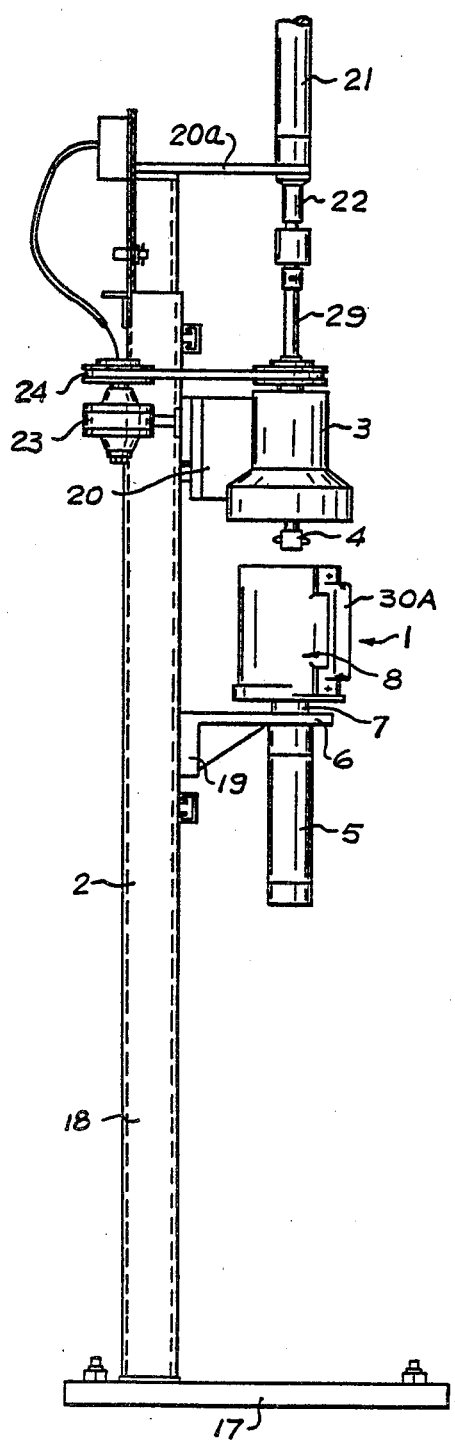
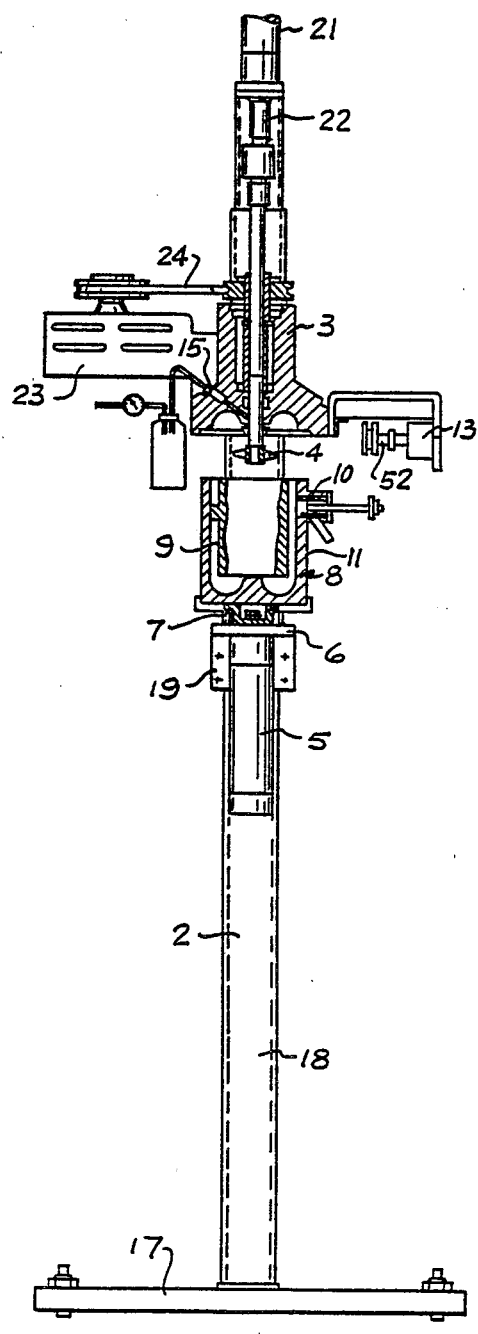

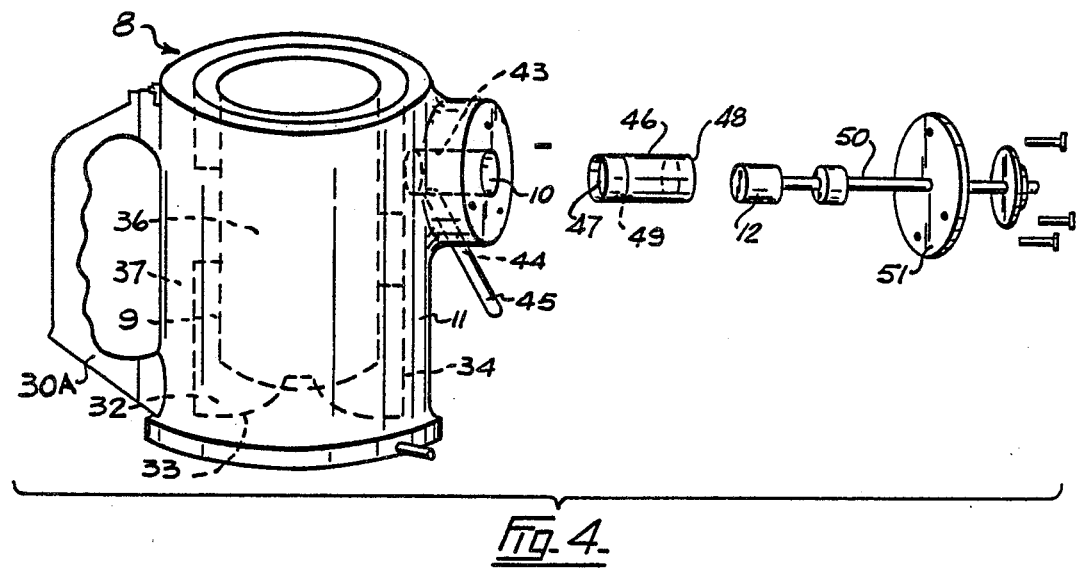
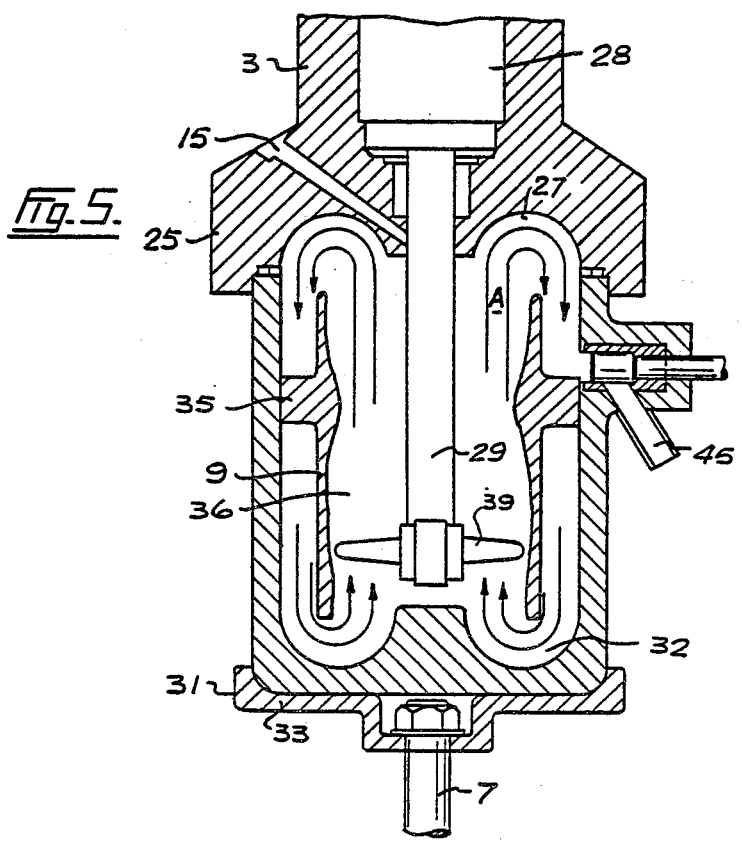

HOMOGENIZER/SUBSAMPLER FOR TAR SAND PROCESS STREAMS

This is a division of application Ser. No. 090,923 filed Nov. 5, 1979 now U.S. Pat. No. 4,284,360.

BACKGROUND OF THE INVENTION

The present invention relates to a homogenizer/subsampler for recovering representative analysis-sized subsamples from a bulk sample which has been taken from a plant process stream. The apparatus finds particular application in connection with the oil-water-solids mixtures encountered in hot water extraction process plants used to recover bitumen from tar sands.

Tar sand typically contains about 12% bitumen, 85% sand and fine solids, and 3% water. Manufacture of synthetic crude from this material only becomes economical at high throughput, since one requires 1 tonne of tar sand to produce ¾ of a barrel of synthetic crude. The hot water extraction process used in this connection has been thoroughly described in the patent literature. A suitable description is given in Canadian Pat. No. 1,055,868, issued to K. C. Porteous et al. As can be seen from such descriptions, tar sand is mixed with hot water and thereafter, by a series of steps, the contained sand and clay solid matter is removed and disposed of in a tailings area and the bitumen is collected, first as a froth and then as substantially pure dry bitumen ready for upgrading.

At different points in the hot water extraction process, streams containing bitumen, water, and solids flow in very large volumes. Those who operate the process require analytical data to ensure that the process is working according to design conditions, that the bitumen reports to the froth, and that only minimal quantities of bitumen are lost to the various tailings streams. Unlike some chemical processes where conditions can be set at a desired optimum, the hot water extraction process must be continually adjusted due to the changing nature of the tar sand feed. It is particularly important that the process be adjusted as the levels of bitumen and fine clay materials in the feedstock vary.

Analytical procedures developed for tar sand streams give results of bitumen, water and solids content of the streams, particle size distribution of the contained solid matter, and characteristics of the bitumen. Such procedures are known to be accurate from the good agreement that can be obtained with identical samples. From the point of view of controlling the process however, accurate analysis alone is not sufficient. It is first necessary that the small sample used for analysis should be representative of the total stream from which it is taken. In many industries this is not a serious problem, either because streams are homogeneous or, where not, because simple subsampling techniques can be used to collect a representative analysis sample. Hence grab sampling, multiple grab sampling, riffling, and continuous withdrawal of a small side stream are well established techniques for reducing a large flow stream volume to an analysis-size volume.

There are difficulties associated with hot water extraction process streams when one comes to trying to obtain representative subsamples for analysis. More particularly, the heavier solid particles rapidly settle out of the mixture; bitumen, being sticky, adheres to any equipment it touches; and the fine clay either remains in contact with the bitumen or remains suspended in the water phase. These problems are complicated when diluent oils, such as naphtha, are included in the streams, largely because of the emulsion-forming tendencies of such diluents. The process streams in the plant vary in composition. Some may be high in bitumen, such as those near the product end of the process, others are high in water, such as the secondary tailings, and still others are high in solids, such as the primary tailings.

There has been a need, therefore, for a means for subsampling hot water extraction process streams in such a way as to provide representative analysis-size subsamples.

The present invention incorporates a structure arrangement known in the prior art. This known structure, used as a homogenizer, involves providing a draft tube coaxially mounted within a vessel. The draft tube is spaced from the vessel walls, so that an elliptical flow path is formed through the bore of the draft tube and the passage between the draft tube and the surrounding vessel. An impellor is provided in the draft tube to drive the vessel contents along the elliptical flow path and homogenize the components of the mixture forming such contents. Typical examples of such prior art homogenizers are shown in U.S. Pat. Nos. 1,351,352 (Stevens), 2,038,221 (Kagi), 3,189,080 (Overcashier), and 4,132,666 (Chikatsu).

SUMMARY OF THE INVENTION

In accordance with the invention, there is provided a homogenizer/subsampler for producing representative analysis-size subsamples of a process stream. The apparatus finds application in connection with those streams of a hot water extraction process plant which contains water, bitumen and solids ranging in particle size from that of coarse sand to that of fine clay.

The apparatus comprises a discrete open-topped vessel, which may be carried by the user to the process line to directly catch the sample. This vessel, filled with the bulk sample, is then combined with the balance of the apparatus to provide the homogenizer/subsampler. The vessel carries internally a generally coaxial draft tube spaced from said vessel's side and base walls. Thus an annular passage is formed between the vessel and the contained draft tube. The volume of the draft tube is preferably generally equal to that of the annular space. The apparatus further comprises support means having means for receiving and holding the vessel. The support means also carries a head element, which is adapted to seal the top opening of the vessel to provide closure thereof. An impellor extends through the head element into the draft tube. This impellor functions to circulate the bulk sample within the vessel. The inside surface of the base of the vessel is preferably partly torroidal in shape. Similarly, the underside of the head element is preferably also partly torroidal. Thus a generally elliptical flow path is defined through the draft tube, the annular passage, and the partly torroidal upper and lower cavities which connect them. The bounding surfaces of this flow path are such that the flow path is free of corners and the like, which would create "dead spots", where solids could collect. A subsampling port extends through the side wall of the vessel so as to communicate with the flow path. Means are provided to pressurize the contents of the vessel. For example, pressurized nitrogen gas can be admitted into the vessel through a port in the head element. Means are also provided to open and close the subsampling port in a closely repeatable manner to permit a subsample to be expelled. Preferably such means may comprise a piston, positioned in the port, and a cylinder for biasing it between open and closed positions to thereby control flow through the port.

In operation, the vessel, containing a subsample, is sealed with the head element. Pressurized gas is admitted and the impellor is actuated to circulate the sample in turbulent flow along the elliptical flow path. The cylinder is then actuated to quickly shift the piston to the open position, to permit a subsample to be discharged through the port, and then to shift it back to the closed position.

The apparatus is characterized by certain advantages. By using the vessel both as the sampling pot and as part of the subsampler, no part of the bulk sample is lost in transferring the sample from one vessel to another. By rapidly circulating the sample, contained solids are substantially uniformly suspended and the components of the mixture are homogenized. By locating the subsampler port along the flow path and providing means which open the port while circulation is in progress, a subsample is obtained which is representative. By providing a flow path whose bounding surfaces do not lend themselves to providing stagnant zones, where concentration and settling of solids may occur, homogeneity is maintained. And by providing a mechanical opening and closing means to control the subsampling port, uniformity of the samples is improved. Previous versions of the apparatus, in which the piston was hand operated, produced subsamples, from a single bulk sample, which varied in composition to an undesirable extent.

Broadly stated, the invention comprises: a discrete open-topped vessel for collecting a bulk sample from which it is required to take one or more representative analysis-size subsamples, said vessel having mounted therein a substantially coaxial draft tube spaced from the vessel side and base walls, thereby forming an annular passage; support means comprising means for supporting the vessel; a head element carried by the support means and operative to seal the top opening of the vessel; means for bringing the vessel and head element together in sealing and closing engagement; said draft tube, head element and vessel combining to form a substantially elliptical flow path extending through the draft tube bore and annular passage; an impellor having a propellor and shaft, said shaft extending through the head element, whereby the propellor is positioned for operation in the draft tube, said shaft being in sealing engagement with the head element; means for driving the impellor to circulate the bulk sample along the flow path; a subsampling port extending through the side wall of the vessel and communicating with the flow path; mechanical means for opening and closing the port for withdrawal of a subsample; and means for pressurizing the bulk sample to cause the subsample to be expelled through the port when said port is in the open position.

In another aspect of the invention, there is provided a method comprising: collecting a bulk sample of the stream in an open-topped vessel; connecting the filled vessel to a head element to enclose the bulk sample; pressurizing the enclosed bulk sample with gas; homogenizing the bulk sample by circulating it along a generally elliptical flow path provided by the vessel and head element; and removing a subsample by opening and closing a port communicating with the flow path while the pressurized bulk sample is in motion.

DESCRIPTION OF THE DRAWINGS

FIG. 1 is a side view of the apparatus;

FIG. 3 is a front view of the apparatus;

FIG. 4 is an exploded view of the vessel, showing the draft tube in shadow lines; and FIG. 5 is a schematic of the head element and vessel, showing the flow path of the contained mixture by way of arrows.

DESCRIPTION OF THE PREFERRED EMBODIMENT

General

Figure 2:
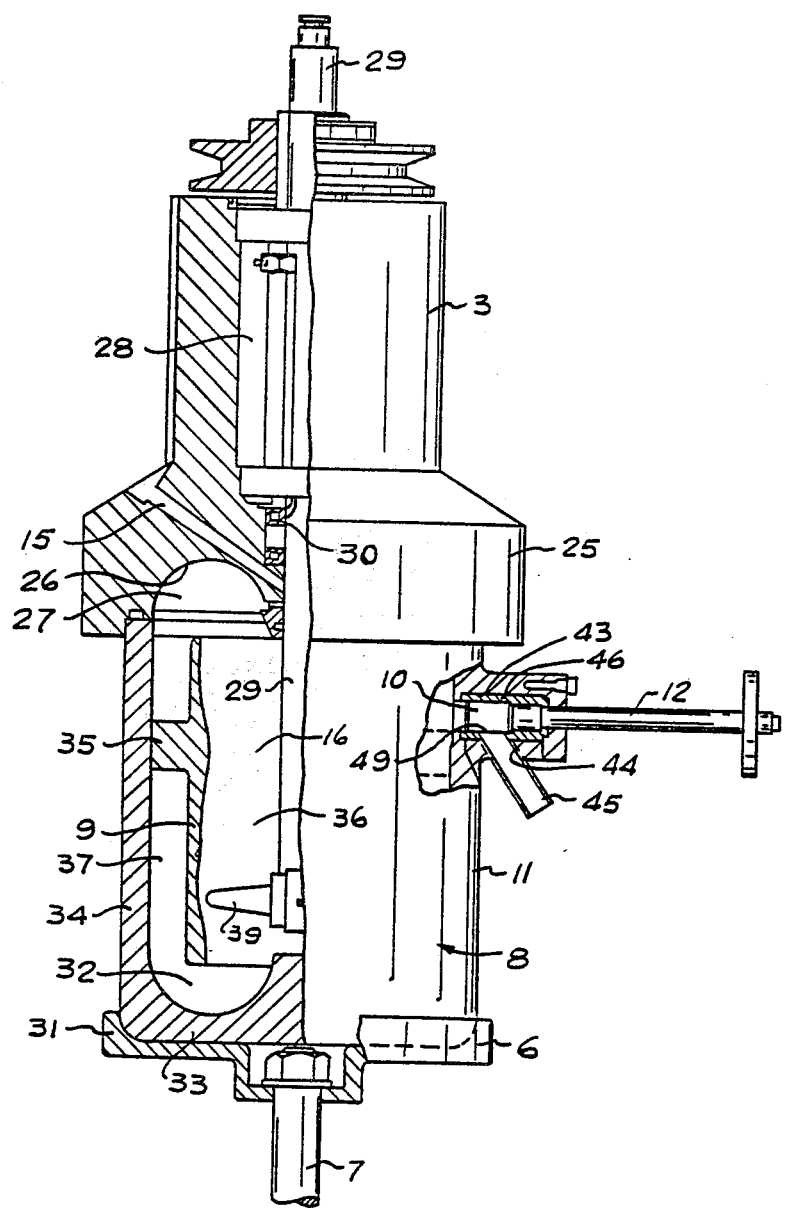
FIG. 2 is a side view, partly broken away, of the vessel and head element.

With reference now to FIGS. 1 and 3, the homogenizer/subsampler 1 comprises support means 2. The support means carries a head element 3. A vertically moveable, driven impellor 4 extends through the head element. The support means 2 also carries a cylinder 5 in spaced relation below the head element 3. A table element 6 is attached to the upper end of the stem 7 of the cylinder 5. A discrete open-topped vessel 8 is supported by the table element 6. Extension of the cylinder 5 brings the vessel 8 into sealing and closing engagement with the head element 3. Turning to the vessel 8, it has a draft tube 9 coaxially mounted therein. A subsampling port 10 extends through the side wall 11 of the vessel 8. A piston 12, actuated by a cylinder 13, is provided to open and close the subsampling port 10. A source (not shown) of pressurizing gas is connected to a bore 15, leading through the head element 3, into the vessel chamber 16.

The Support Means

The support means 2 comprises a base 17 and an upright 18, from which are suspended, directly or indirectly, the components of the apparatus. More particularly, the upright 18 has attached thereto a bracket 19 supporting the vertical cylinder 5. The horizontal table element 6 is mounted on the upper end of the stem 7 of the cylinder 5, for supporting the sample-collecting vessel 8. A second bracket 20 extends from the upright 18 and is attached to the head element 3, so that the latter is positioned directly above the table element 6 in spaced relation. A third bracket 20a is connected with the upright 18 and carries a cylinder 21, whose stem 22 is connected with and biases the impellor 4 in a downward direction. The support means 2 further carries a motor 23 which drives the impellor 4 through the belt 24.

While the embodiment shown in the drawings has all the components of the apparatus suspended from a single upright, it is self-evident that some of the components could be separately supported.

The Head Element

With reference to FIG. 2, the head element 3 has a base portion 25 whose underside 26 is formed to provide a smooth, partly torroidal cavity 27. By partly torroidal is meant that the shape of the cavity is substantially that of the curved surface of a doughnut cut through its longest plane.

A central bore 28 extends downwardly through the head element 3. The impellor shaft 29 extends through this bore 28. Seals 30 seal the shaft 29 with the head element 3.

Means for Pressurizing

A bore 15 extends through the side wall of the head element 3 to a point below the seals 30. An inert gas, such as nitrogen, may be introduced into the vessel 8 from the source 14 through the bore 15, to pressurize the bulk sample contained in the vessel 8.

The Sample-Collecting Vessel

The vessel 8 is cylindrical and open-topped. It has a handle 30A and is sized to be received and retained by the peripheral upstanding rim 31 of the table element 6. A partly torroidal cavity 32 is formed in the inner side of its base wall 33.

A cylindrical draft tube 9 is substantially coaxially mounted within the vessel in spaced relation with its side and base walls 34,33. The draft tube 9 may have a constriction 35 along its length to create a venturi effect and assist in developing turbulence of the mixture.

A substantially elliptical flow path A, outlined by the arrows in FIG. 5, is thus created through the bore 36 of the draft tube 9, the upper partly torroidal cavity 27, the annular passage 37 between the draft tube 9 and the vessel side wall 11, and the lower torroidal cavity 32.

The Impellor

The impellor 4 comprises a shaft 29 carrying a marine-type propellor 39 at its lower end. This shaft 29 is attached to the stem 22 of the cylinder 21 at its upper end. Thus the propellor 39 may be lowered to the base of the draft tube 9.

The propellor 39 preferably extends outwardly close to the inside surface of the draft tube 9. Otherwise, the portion of the bulk sample near the draft tube wall is agitated less than the balance of the mixture with the result that solids may settle out and heavy oil adhere to the wall.

It is desirable that the impellor 4 be vertically moveable. Thus the propellor 39 may be rotated as it begins to penetrate the mixture. If the propellor is placed at full depth before being set in motion, settled solids will exert a drag on the drive motor 23, which may be damaging to it.

The propellor 39 preferably is shaped to circulate the sample mixture upwardly through the draft tube 9 and downwardly through the annular passage 37. If it were otherwise, there would be a tendency to form a bed of compacted solids in the bottom of the vessel.

Subsampling Port and Control Means

As previously stated, a subsampling port 10 extends through the side wall 11 of the vessel 8. The port 10 communicates with the flow path A. In the embodiment shown in FIG. 4, the port 10 comprises a horizontal bore 43 and a downwardly extending bore 44, which terminates in an open-ended tubular spout 45. The bore 44 communicates with the bore 43 part way along the length of the latter.

A sleeve 46 fits snugly within the bore 43. At its inner end, the sleeve 46 carries an internally mounted O-ring 47. Toward its outer end, the sleeve 46 carries an externally mounted O-ring 48. An aperture 49 extends through the sleeve wall at a point between the O-rings 47, 48 so as to communicate with the bore 44.

A piston 12 is positioned in the sleeve 46. The shaft 50 of the piston extends through a cover 51 which is screwed to the vessel 8. The piston 12 is shiftable between a closed position, wherein it seals the bore 43 from the annular passage 37 by engaging the O-ring 47, and an open position, wherein it is positioned to the rear of the aperture 49, thereby permitting a subsample to be expelled through the bores 43 and 44.

The shaft 50 of the piston 12 is engaged by the stem 52 of the cylinder 13. The cylinder 13 may be actuated to shift the piston 12 between the open and closed positions in a consistent or closely repeatable manner for rapid withdrawal of a subsample.

The driving components of the apparatus may be actuated manually or with automatic means.

Operation

The bulk sample is caught in the vessel 8 which is then placed on the table element 6. The cylinder 5 is extended to bring the head element 3 and vessel 8 into sealing and closing engagement. Pressure is applied to the bulk sample by introducing pressurized nitrogen into the vessel 8 through the bore 15. The impellor 4 is then actuated and lowered, while rotating, to the base of the draft tube 9. The bulk sample is circulated in turbulent fashion along the flow path A. When desired, the piston 12 may be withdrawn and then advanced to permit a subsample to be expelled while the bulk sample is in motion.

Operating characteristics of the apparatus are demonstrated by the following examples.

EXAMPLE I

Tests to determine the mixing effectiveness were carried out on streams of a pilot plant for the extraction of bitumen from tar sand. The raw tar sand typically analyses at about 12% bitumen (a highly viscous heavy oil), 85% mineral particles (ranging in size from beach sand grains down to clay particles of diameter less than 1 micron), and 3% water (with some dissolved salts), all values being by weight. Shortly stated, the hot water process, which is the process currently in commercial use, involves agitating the tar sand feed with water at about 80° C., adding further hot water, advancing the flooded slurry so produced to a quiescent zone (primary separation vessel) where a bitumen-rich froth (primary froth) floats to the surface; a substantially bitumen-free sand is pumped with water from the bottom of the vessel (primary tailings); and a "middlings" stream of water, small bitumen globules, and clay minerals is advanced to induced air flotation cells. These cells in turn produce a further yield of bituminous froth (secondary froth) from which excess water is allowed to settle in a cleaner to produce cleaner froth and secondary tailings. Commonly the primary and secondary froths are combined, treated with a light hydrocarbon solvent to dilute the bitumen, and the hydrocarbon phase is separated out of the mixture, for instance by centrifugation.

As can be seen, the various streams are mixtures of hydrocarbons, solids, and water, which present serious difficulties in the taking of representative samples and subsamples.

One set of tests was done on cleaner froth, middlings, and secondary tailings. In all cases, for plant work, results ranging within ±5% of the absolute value for each component were required from the subsampler. To get absolute readings the whole stream was diverted long enough to collect an analysis-size sample. Three such samples were taken at the beginning of the test and three at the end and the results for all six determinations of water and solids content were averaged. A bulk sample was also taken directly into the mixing vessel of the homogenizer/subsampler hereindescribed, mixed in the prescribed manner, and subsampled five times via the subsampling port. Oil, water, and solids were determined on the five subsamples and the results averaged. Table 1 shows the average for each component of each stream and the range of values expressed as plus or minus (±). As can be seen, the subsampler values are well within the ±5% specified in all cases and the subsampler values for oil and water in secondary froth are strikingly better than the range obtained from taking whole stream samples.

It is emphasized that the whole flow samples were taken from the pilot plant for experimental purposes only. Short-period diversion of the whole stream should, ideally, give absolute values especially when, as done here, several samples are taken in rapid succession and the analytical results averaged. It will be noted that even under these arrangements, use of the homogenizer/subsampler led to superior results. At the commercial level however such diversion of a whole stream is rarely possible because of the large volume of such streams, and a subsampling device is hence essential.

TABLE 1

MEAN ASSAYS

| Stream | % OIL St. Dev. | % WATER St. Dev. | % SOLIDS St. Dev. |
|---|---|---|---|
| Secondary Froth | | | |
| Whole Stream | 25.77 ± 7.47 | 61.22 ± 7.77 | 11.23 ± 0.40 |
| Relative Standard Deviation | ± 28.99 | ± 12.69 | ± 3.56 |
| Subsampler | 27.06 ± 1.19 | 61.40 ± 0.79 | 11.54 ± 0.43 |
| Relative Standard Deviation | ± 4.40 | ± 1.29 | ± 3.73 |
| Middlings | | | |
| Whole Stream | 8.37 ± 0.19 | 70.72 ± 0.34 | 20.91 ± 0.30 |
| Relative Standard Deviation | ± 2.27 | ± 0.48 | ± 1.43 |
| Subsampler | 8.39 ± 0.17 | 70.83 ± 0.58 | 20.78 ± 0.59 |
| Relative Standard Deviation | ± 2.03 | ± 0.82 | ± 2.84 |
| Secondary Tailings | | | |
| Whole Stream | 0.67 ± 0.04 | 76.27 ± 1.23 | 23.07 ± 1.20 |
| Relative Standard Deviation | ± 5.97 | ± 1.61 | ± 5.20 |
| Subsampler | 0.69 ± 0.04 | 76.38 ± 1.04 | 22.94 ± 1.04 |
| Relative Standard Deviation | ± 5.80 | ± 1.36 | ± 4.53 |

EXAMPLE II

To test the subsampling step in automatic mode (that is operating the piston 12 mechanically instead of manually), middlings and combined tailings were taken in the mixing vessel of the homogenizer/subsampler and replicate subsamples were withdrawn after 5 minutes mixing with the agitator at 1600 r.p.m. Average subsample weight was 54.76 g for 9 subsamples of middlings, and 49.85 g for 7 subsamples of combined tailings. The results are shown in Table 2, where standard deviation ranges from 0.04 to 0.25 show the excellent precision. The results for middlings have lower deviation when the sample port is operated mechanically instead of manually.

TABLE 2

REPLICATE ASSAY RESULTS - SEMI AUTOMATED SUBSAMPLER 1600 RPM, 5 Min HOMOGENIZATION

| | % Oil | % Water | % Solids | |
|---|---|---|---|---|
| Middlings | | | | |
| | 7.92 | 71.63 | 20.45 | |
| | 7.96 | 71.58 | 20.45 | |
| | 7.93 | 71.56 | 20.51 | |
| | 7.96 | 71.71 | 20.33 | |
| | 7.87 | 71.97 | 20.15 | |
| | 8.04 | 71.91 | 20.04 | |
| | 8.08 | 71.89 | 20.03 | |
| | 8.05 | 71.93 | 20.02 | |
| | 8.20 | 72.00 | 19.80 | |
| $\bar{x}$ | 8.00 | 71.80 | 20.20 | Average |
| $\sigma$ | 0.10 | 0.18 | 0.25 | Subsample Weight 54.76 g |
| Relative Standard Deviation | 1.26% | 0.25% | 1.22% | |
| Combined Tailings | | | | |
| | 1.36 | 44.25 | 54.39 | |
| | 1.46 | 44.19 | 54.35 | |
| | 1.48 | 44.28 | 54.24 | |
| | 1.44 | 44.07 | 54.48 | |
| | 1.45 | 43.75 | 54.80 | |
| | 1.41 | 43.94 | 54.65 | |
| | 1.46 | 43.63 | 54.91 | |
| $\bar{x}$ | 1.44 | 44.02 | 54.55 | Average |
| $\sigma$ | 0.04 | 0.25 | 0.25 | Subsample Weight 49.85 g |
| Relative Standard Deviation | 2.80% | 0.57% | 0.45% | |

The embodiments of the invention in which an exclusive property or privilege is claimed are defined as follows:

1. A method of subsampling a tar sands hot water extraction plant stream comprising:
   collecting a bulk sample of the stream in an open-topped vessel;
   connecting the filled vessel to a head element to enclose the bulk sample;
   pressurizing the enclosed bulk sample with gas;
   homogenizing the bulk sample by circulating it along a generally elliptical flow path provided by the vessel and head element; and
   removing a subsample by opening and closing a port communicating with the flow path while the pressurized bulk sample is in motion.

* * * * *